(12) United States Patent
Tsang et al.

(10) Patent No.: US 12,318,274 B2
(45) Date of Patent: Jun. 3, 2025

(54) METHOD OF MAKING AN ABSORBENT COMPOSITE

(71) Applicant: DSG Technology Holdings Ltd., Kwai Chung (HK)

(72) Inventors: Patrick King Yu Tsang, Tuen Mun (HK); Kuo-Shu Edward Chang, Charlotte, NC (US); Andrew C. Wright, Chesterfield (GB)

(73) Assignee: DSG Technology Holdings LTD, Kwai Chung (HK)

( * ) Notice: Subject to any disclaimer, the term of this patent is extended or adjusted under 35 U.S.C. 154(b) by 1194 days.

(21) Appl. No.: 17/030,985

(22) Filed: Sep. 24, 2020

(65) Prior Publication Data

US 2021/0077320 A1   Mar. 18, 2021

Related U.S. Application Data

(60) Division of application No. 15/584,675, filed on May 2, 2017, now Pat. No. 10,864,121, which is a
(Continued)

(51) Int. Cl.
 *A61F 13/15* (2006.01)
 *A61F 13/494* (2006.01)
 (Continued)

(52) U.S. Cl.
 CPC ...... *A61F 13/539* (2013.01); *A61F 13/15658* (2013.01); *A61F 13/15699* (2013.01);
 (Continued)

(58) Field of Classification Search
 None
 See application file for complete search history.

(56) References Cited

U.S. PATENT DOCUMENTS 3,071,138 A   1/1963   Garcia
3,670,731 A   6/1972   Harmon
(Continued)

FOREIGN PATENT DOCUMENTS

EP   0212618 A1   3/1987
EP   0725616 B1   3/1999
(Continued)

OTHER PUBLICATIONS

KR 20000048805; Jul. 25, 2000, Payne et al. (Year: 2000).*
(Continued)

*Primary Examiner* — Barbara J Musser
(74) *Attorney, Agent, or Firm* — Alberto Q. Amatong, Jr.; Amatong McCoy LLC

(57) ABSTRACT

A method of making an absorbent composite that includes a first fabric, a second fabric, and particles positioned between the two fabrics and absorbent articles made from the absorbent composite. The particles are secured between the two fabric using adhesive, thermal plastic or combinations thereof. The fabrics are bonded together in a manner that limits particle movement between the fabrics. The bond pattern may define pockets or other shapes. In applications in which the bond pattern forms pockets, the particles may be positioned in the pockets. The particles may be SAP particles or other particles with advantageous properties.

30 Claims, 11 Drawing Sheets

Related U.S. Application Data continuation of application No. 14/134,001, filed on Dec. 19, 2013, now Pat. No. 9,757,284, which is a continuation of application No. 13/424,041, filed on Mar. 19, 2012, now Pat. No. 9,561,139, which is a division of application No. 11/360,115, filed on Feb. 22, 2006, now Pat. No. 8,148,598.

(51) Int. Cl.
*A61F 13/514* (2006.01)
*A61F 13/532* (2006.01)
*A61F 13/536* (2006.01)
*A61F 13/539* (2006.01)
A61F 13/53 (2006.01)
A61F 13/535 (2006.01)

(52) U.S. Cl.
CPC .. *A61F 13/49426* (2013.01); *A61F 13/51405* (2013.01); *A61F 13/51478* (2013.01); *A61F 13/5323* (2013.01); *A61F 13/536* (2013.01); *A61F 13/15577* (2013.01); *A61F 13/15764* (2013.01); *A61F 2013/530554* (2013.01); *A61F 2013/530562* (2013.01); *A61F 2013/530671* (2013.01); *A61F 2013/5307* (2013.01); *A61F 2013/5355* (2013.01); *A61F 2013/53925* (2013.01); *Y10T 156/10* (2015.01)

(56) References Cited

U.S. PATENT DOCUMENTS

| | | |
|---|---|---|
| 3,780,399 A | 12/1973 | Morel |
| 3,814,100 A | 6/1974 | Nystrand et al. |
| 4,055,180 A | 10/1977 | Karami |
| 4,100,324 A | 7/1978 | Anderson et al. |
| 4,360,021 A | 11/1982 | Stima |
| 4,381,783 A | 5/1983 | Elias |
| 4,434,010 A | 2/1984 | Ash |
| 4,571,924 A | 2/1986 | Bahrani |
| 4,646,362 A | 3/1987 | Heran et al. |
| 4,670,011 A | 6/1987 | Mesek |
| 4,673,402 A | 6/1987 | Weisman et al. |
| 4,699,823 A | 10/1987 | Kellenberger et al. |
| 4,715,918 A | 12/1987 | Lang |
| 4,820,577 A | 4/1989 | Morman et al. |
| 4,960,477 A | 10/1990 | Mesek |
| 4,994,053 A | 2/1991 | Lang |
| 5,008,143 A | 4/1991 | Armanini |
| 5,030,314 A | 7/1991 | Lang |
| 5,037,412 A | 8/1991 | Tanzer et al. |
| 5,094,717 A | 3/1992 | Manning et al. |
| 5,098,423 A | 3/1992 | Pieniak et al. |
| 5,118,376 A | 6/1992 | Pigneul et al. |
| 5,122,407 A | 6/1992 | Yeo et al. |
| 5,149,335 A | 9/1992 | Kellenberger et al. |
| 5,281,207 A | 1/1994 | Chmielewski et al. |
| 5,294,478 A | 3/1994 | Wanek et al. |
| 5,336,552 A | 8/1994 | Strack et al. |
| 5,342,333 A | 8/1994 | Tanzer et al. |
| 5,350,370 A | 9/1994 | Jackson et al. |
| 5,364,380 A | 11/1994 | Tanzer et al. |
| 5,411,497 A | 5/1995 | Tanzer et al. |
| 5,425,725 A | 6/1995 | Tanzer et al. |
| 5,433,715 A | 7/1995 | Tanzer et al. |
| 5,436,066 A | 7/1995 | Chen |
| 5,458,592 A | 10/1995 | Abuto et al. |
| 5,482,761 A | 1/1996 | Palumbo et al. |
| 5,494,622 A | 2/1996 | Heath et al. |
| 5,505,718 A | 4/1996 | Roe et al. |
| H1565 H | 7/1996 | Brodof et al. |
| H1585 H | 8/1996 | Ahr |
| 5,549,589 A | 8/1996 | Horney et al. |
| 5,562,645 A | 10/1996 | Tanzer et al. |
| 5,562,646 A | 10/1996 | Goldman et al. |
| 5,567,744 A | 10/1996 | Nagata et al. |
| 5,591,149 A | 1/1997 | Cree et al. |
| 5,593,399 A | 1/1997 | Tanzer et al. |
| 5,599,335 A | 2/1997 | Goldman et al. |
| 5,601,542 A | 2/1997 | Melius et al. |
| 5,650,222 A | 7/1997 | DesMarais et al. |
| 5,653,702 A | 8/1997 | Brohammer et al. |
| 5,669,894 A | 9/1997 | Goldman et al. |
| 5,695,486 A | 12/1997 | Broughton et al. |
| 5,749,259 A | 5/1998 | Hamouda et al. |
| 5,763,331 A | 6/1998 | Demhartner |
| 5,782,819 A | 7/1998 | Tanzer et al. |
| 5,788,684 A | 8/1998 | Abuto et al. |
| 5,800,418 A | 9/1998 | Ahr |
| 5,810,796 A | 9/1998 | Kimura et al. |
| 5,821,179 A | 10/1998 | Masaki et al. |
| 5,853,403 A | 12/1998 | Tanzer et al. |
| 5,863,288 A | 1/1999 | Baker |
| 5,938,650 A | 8/1999 | Baer et al. |
| 5,941,862 A | 8/1999 | Haynes et al. |
| 5,944,706 A | 8/1999 | Palumbo et al. |
| 5,947,947 A | 9/1999 | Tanzer et al. |
| 6,024,822 A | 2/2000 | Alper et al. |
| 6,046,377 A | 4/2000 | Huntoon et al. |
| 6,068,620 A | 5/2000 | Chmielewski |
| 6,071,549 A | 6/2000 | Hansen |
| 6,086,950 A | 7/2000 | Masaki et al. |
| 6,093,474 A | 7/2000 | Sironi |
| 6,129,720 A | 10/2000 | Blenke et al. |
| 6,140,550 A | 10/2000 | Beihoffer et al. |
| 6,152,906 A | 11/2000 | Faulks et al. |
| 6,162,959 A | 12/2000 | O'Connor |
| 6,177,607 B1 | 1/2001 | Blaney et al. |
| 6,238,379 B1 | 5/2001 | Keuhn et al. |
| H1969 H | 6/2001 | Fell et al. |
| 6,241,713 B1 | 6/2001 | Gross et al. |
| 6,245,693 B1 | 6/2001 | Gagliardi et al. |
| 6,258,076 B1 | 7/2001 | Glaug et al. |
| H1978 H | 8/2001 | Freiburger et al. |
| 6,290,686 B1 | 9/2001 | Tanzer |
| 6,329,565 B1 | 12/2001 | Dutkiewicz et al. |
| 6,392,116 B1 | 5/2002 | Beihoffer et al. |
| 6,420,626 B1 | 7/2002 | Erspamer et al. |
| 6,429,350 B1 | 8/2002 | Tanzer et al. |
| 6,448,464 B1 | 9/2002 | Akin et al. |
| 6,458,877 B1 | 10/2002 | Ahmed et al. |
| 6,491,677 B1 | 12/2002 | Glaug et al. |
| 6,500,251 B1 | 12/2002 | Andes et al. |
| 6,534,572 B1 | 3/2003 | Ahmed et al. |
| 6,548,732 B2 | 4/2003 | Erdman et al. |
| 6,569,137 B2 | 5/2003 | Suzuki et al. |
| 6,570,056 B1 | 5/2003 | Tanzer et al. |
| 6,610,900 B1 | 8/2003 | Tanzer |
| 6,632,209 B1 | 10/2003 | Chmielewski |
| 6,645,407 B2 | 11/2003 | Kellenberger et al. |
| 6,680,423 B1 | 1/2004 | Tanzer |
| 6,689,205 B1 | 2/2004 | Brückner et al. |
| 6,689,934 B2 | 2/2004 | Dodge et al. |
| 6,700,035 B2 | 3/2004 | Yoshimasa |
| 6,702,800 B1 | 3/2004 | Vukos et al. |
| 6,730,069 B2 | 5/2004 | Tanzer et al. |
| 6,790,798 B1 | 9/2004 | Suzuki et al. |
| 6,797,360 B2 | 9/2004 | Varona |
| 6,849,672 B2 | 2/2005 | Mehawej et al. |
| 6,875,264 B2 | 4/2005 | Zimmermann et al. |
| 6,878,433 B2 | 4/2005 | Curro et al. |
| 6,899,776 B2 | 5/2005 | Bahlmann et al. |
| 6,965,058 B1 | 11/2005 | Raidel et al. |
| 6,972,011 B2 | 12/2005 | Maeda et al. |
| 7,321,007 B2 | 1/2008 | Gagliardi et al. |
| 7,722,590 B2 | 5/2010 | Tsuji et al. |
| 7,744,576 B2 | 6/2010 | Busam et al. |
| 7,750,203 B2 | 7/2010 | Becker et al. |
| 7,759,540 B2 | 7/2010 | Litvay et al. |
| 7,767,878 B2 | 8/2010 | Suzuki |
| 7,838,721 B2 | 11/2010 | Chen |
| 7,838,722 B2 | 11/2010 | Blessing et al. |
| 7,847,145 B2 | 12/2010 | Kurita et al. |
| 7,872,168 B2 | 1/2011 | Sawyer et al. |

(56) References Cited

U.S. PATENT DOCUMENTS

| | | |
|---|---|---|
| 7,994,233 B2 | 8/2011 | Mehawej et al. |
| 7,994,384 B2 | 8/2011 | Qin et al. |
| 8,163,124 B2 | 4/2012 | Moriura et al. |
| 8,187,240 B2 | 5/2012 | Busam et al. |
| 8,211,076 B2 | 7/2012 | Sugiyama et al. |
| 8,735,646 B2 | 5/2014 | Beruda et al. |
| 8,901,367 B2 | 12/2014 | Sanz et al. |
| 2003/0119394 A1 | 6/2003 | Ranganathan et al. |
| 2003/0119402 A1 | 6/2003 | Melius et al. |
| 2003/0120231 A1 | 6/2003 | Wang et al. |
| 2003/0129915 A1 | 7/2003 | Harriz |
| 2003/0149414 A1 | 8/2003 | Mehawej |
| 2003/0175418 A1 | 9/2003 | Muthiah et al. |
| 2004/0015142 A1 | 1/2004 | Johnston et al. |
| 2004/0054342 A1 | 3/2004 | Newbill et al. |
| 2004/0116014 A1 | 6/2004 | Soerens et al. |
| 2004/0167486 A1 | 8/2004 | Busam et al. |
| 2004/0204697 A1 | 10/2004 | Litvay |
| 2005/0166799 A1 | 8/2005 | Fuller et al. |
| 2005/0171499 A1 | 8/2005 | Nigam et al. |
| 2006/0004334 A1 | 1/2006 | Schlinz et al. |
| 2006/0021695 A1 | 2/2006 | Blessing et al. |
| 2006/0278335 A1 | 12/2006 | Moriura et al. |
| 2007/0093164 A1 | 4/2007 | Nakaoka |
| 2009/0076473 A1 | 3/2009 | Kasai et al. |

FOREIGN PATENT DOCUMENTS

| | | | |
|---|---|---|---|
| EP | 1447066 A1 | 8/2004 | |
| EP | 1447067 A1 | 8/2004 | |
| EP | 1561442 A1 | 8/2005 | |
| EP | 1609448 A1 | 12/2005 | |
| EP | 1627618 A1 | 2/2006 | |
| EP | 1655007 A1 | 5/2006 | |
| GB | 2252047 A | 7/1992 | |
| JP | 106190001 A | 7/1994 | |
| JP | 07132126 | 5/1995 | |
| JP | 7246366 | 9/1995 | |
| JP | 08246395 | 9/1996 | |
| JP | 10118115 | 5/1998 | |
| JP | 2000238161 A | 9/2000 | |
| JP | 2002159533 A | 6/2002 | |
| JP | 2002345883 A | 12/2002 | |
| JP | 2004358797 A | 12/2004 | |
| WO | 9503019 A1 | 2/1995 | |
| WO | 9521596 A1 | 8/1995 | |
| WO | 9705841 A1 | 2/1997 | |
| WO | 2004098473 A1 | 11/2004 | |
| WO | WO-2005011548 A1 * | 2/2005 | ....... A61F 13/15658 |
| WO | 2006007185 A1 | 1/2006 | |
| WO | 2006015138 A1 | 2/2006 | |

OTHER PUBLICATIONS

1st Office Action from Canadian Application No. 2,643,482, dated Oct. 30, 2013; 3 pages.

2nd Office Action from Canadian Application No. 2,643,482, dated Jun. 20, 2014; 2 pages.

2nd Office Action from Chinese Application No. 200780014162.9 filed Feb. 22, 2007, dated Aug. 29, 2012, 7pages.,.

3rd Office Action from Chinese Application No. 200780014162.9 filed Feb. 22, 2007, dated Feb. 27, 2013, 8 pages.

4th Office Action from Chinese Application No. 200780014162.9, dated Aug. 9, 2013; 14 pages.

Decision on Rejection from Chinese Application No. 200780014162. 9, dated Dec. 4, 2013; 16 pages.

International Preliminary Report on Patentability issued and published Aug. 26, 2008, during the prosecution of International Application No. PCT/US2007/062614.

International Search Report Issued Dec. 17, 2007, and published Feb. 21, 2008, during the prosecution of International Application No. PCT/US2007/062614.

Office Action from Chinese Application No. 200780014162.9 filed Feb. 22, 2007, dated Feb. 29, 2012, 9 pages.

U.S. Appl. No. 60/652,020, Fuller et al.

Written Opinion issued Dec. 17, 2007, and published Aug. 22, 2008 during the prosecution of International Application No. PCT/US2007/062614.

* cited by examiner a b c d e f g h i j k

METHOD OF MAKING AN ABSORBENT COMPOSITE

The present application is a Divisional of U.S. application Ser. No. 15/584,675, filed on May 2, 2017 (now U.S. Pat. No. 10,864,121), which is a Continuation of U.S. patent application Ser. No. 14/134,001, filed Dec. 19, 2013 (now U.S. Pat. No. 9,757,284), which is a Continuation of U.S. patent application Ser. No. 13/424,041, filed Mar. 19, 2012 (now U.S. Pat. No. 9,561,139), which is a Divisional of U.S. patent application Ser. No. 11/360,115, filed Feb. 22, 2006 (now U.S. Pat. No. 8,148,598), (which is hereby incorporated by reference for all purposes and made a part of the present disclosure).

BACKGROUND OF THE INVENTION

The present invention relates generally to a method of making an absorbent composite. The present invention also relates generally to disposable absorbent articles employing absorbent composites. Disposable absorbent articles include diapers, training pants, adult incontinence products, bodily exudates absorbing products, feminine hygiene products, and other absorbent products (collectively "disposable absorbent articles").

Prior disposable absorbent articles typically employ three basic structural elements: a topsheet that forms the inner surface, a backsheet that forms the outer surface, and an absorbent core that is interposed between the topsheet and the backsheet. The topsheet is designed to allow liquid to pass from outside the absorbent article through the topsheet and into the absorbent core. The topsheet may be made out of a range of liquid and vapor permeable hydrophilic or hydrophobic materials. The permeability of the topsheet can be increased by using surface activation agents ("surfactants"). Surfactants lower the surface energy or the contact angle of the liquid-solid interface and facilitate the liquid's passage through the topsheet.

The backsheet is designed to prevent fluid from passing from the absorbent core through the backsheet and out of the absorbent article. The backsheet may be made out of an impermeable film that extends the full width of the article or a combination of cloth-like material and impermeable film. The backsheet may also have vapor transmission properties ("breathability") that allow vapor to pass through the backsheet without releasing fluid stored in the absorbent core. The backsheet may also be made from a liquid impermeable but vapor transmittable non-woven material such as spunbond, melt-blow, spun-bond ("SMS"); spun-bond, melt-blown, melt-blown, spun-bond ("SMMS"); micro, nano, or splitable fibers; spun melt or spun laced; carded; and the like.

The absorbent core is designed to contain and distribute fluid that passes through the topsheet. A typical absorbent core is made out of a high or super absorbent polymer (SAP) stabilized by an absorbent matrix. SAP is commonly made out of materials such as polyvinyl alcohol, polyacrylates, various grafted starches, and cross-linked sodium polyacrylate. SAP can be in the form of particles, fibers, foams, web, spheres, agglomerates of regular or irregular shapes, and film. The absorbent matrix is typically a de-fiberized wood pulp or similar material. The absorbent matrix is very bulky relative to the topsheet, backsheet, and SAP. Most of a diaper's thickness comes from the absorbent core.

Increasingly, consumers of absorbent articles are demanding thinner absorbent articles. To meet these demands, manufactures are decreasing the thickness of absorbent articles by decreasing the amount of absorbent matrix used in absorbent cores. Although the resulting absorbent cores are thinner, they suffer in performance. As the amount of absorbent matrix is reduced, it is less effective in stabilizing the SAP-preventing the SAP from migrating within the absorbent core. As SAP migrates within the core, the absorbent core losses its effectiveness and no longer has uniform absorbency. For example, SAP that is not contained tends to bunch up in wetted areas and is inefficient for handling subsequent discharges.

Manufactures have attempted to solve this problem by creating small, individual SAP pockets or by gluing the SAP. These solutions, however, have been largely unsuccessful. The SAP pockets merely limit the migration to movement within the pockets. However, because there is still a movement of the particles, the absorbent core does not exhibit uniform absorbency. Gluing the SAP stabilizes the SAP, but results in an uncomfortably stiff absorbent core and a loss in the SAP's swelling capacity.

Accordingly, there exists a need for an improved absorbent product that continues the trend of decreasing product thickness, while minimizing product stiffness and otherwise exhibiting excellent absorbency.

BRIEF SUMMARY OF THE INVENTION

The present invention discloses an absorbent composite that does not require an absorbent matrix and a novel method of making the absorbent composite. The present invention also discloses an absorbent article that incorporate the absorbent composite. The novel absorbent composite described herein provides for an absorbent article that can be made very thin and pliable, while at the same time retaining enough SAP to provide sufficient absorbency and dry and wet integrity (uniform absorbency). Although using the absorbent composite in a diaper is described, one skilled in the art would readily understand that an absorbent composite made according to the inventive process may be used in a wide variety of absorbent products.

The present invention is also directed to an improved absorbent article incorporating the novel absorbent composite.

One embodiment of the present invention is a method of manufacturing a composite sheet, comprising the steps of positioning a first fabric to receive particles, depositing particles on the first fabric, applying adhesive to a second fabric, positioning the second fabric relative to the first fabric, and forming bond sites that extend between the first and second fabric. The inventive method may further include an article in which the particles comprise SAP particles, skin care particles, odor absorbing particles, binder particles, ion exchange particles, and combinations thereof. Still further, the inventive method may include the step of coating the particles with a hydrophobic material.

The inventive method may include the step of conforming the first fabric to a surface. The surface may include recesses that form pockets in the first fabric when it is conformed to the surface. The SAP particles may be guided into the pockets formed in the first fabric. Suction may be used to conform the first fabric to the surface. The adhesive applied to the second fabric may be applied in a concentration sufficient to secure an effective amount of dry particles. That concentration is generally between 1 to 100 grams per square meter. More specifically, the adhesive may be applied in a concentration of between 5 and 75 grams per square meter, or even more optimally, between 12 and 50 grams per square meter. The adhesive may be applied in a manner such that the total amount of adhesive engaging particles is between 1 and 100 grams per square meter. The inventive method may further includes a step of applying adhesive to the first fabric before particles are deposited on the first fabric.

The bond sites of the inventive method may be bond lines, which may be continuous or discontinuous and may define pockets or other shapes and designs. Alternatively, the bond sites may be bond points. The bond sites of the inventive method may be positioned relative to particles and/or arranged to prevent straight line particle migration of more than 2 inches.

An alternative embodiment of the inventive method comprising the steps of positioning a first fabric to receive particles, positioning particles on the first fabric, securing the particles relative to the first fabric, positioning a second fabric over the particles, and forming bond sites that join the first fabric to the second fabric. The bond sites may be discrete points spaced to inhibit the migration of particles. The bond sites may also be bond lines spaced to inhibit the migration of particles, or bond lines that are connected to form a single bond line. The bond lines may be arranged to form pockets within which some particles are positioned. The particles may be SAP particles, skin care particles, odor absorbing particles, binder particles, ion exchange particles, and combinations thereof. The particles may be secured to the first fabric with adhesive, thermal plastic, or combinations thereof. In addition to or in the alternative, the particles may be secured to the second fabric with adhesive, thermal plastic, or combinations thereof. The alternative embodiment may further include the step of forming shapes in the first fabric for receiving particles.

A novel disposable absorbent article according to the present invention comprises a topsheet, a backsheet, and an absorbent core disposed therebetween, wherein at least a portion of one of the backsheet, topsheet, and absorbent core is an absorbent composite comprising a first fabric, a second fabric bonded to the first fabric, and particles adhered between the first and second fabric. The particles may be SAP particles, skin care particles, odor absorbing particles, binder particles, ion exchange particles, and combinations thereof.

The novel article may further include a pair of longitudinally extending, upstanding cuffs spaced laterally from the core, each the cuff including a folded portion of the topsheet and a longitudinally-extending absorbent composite secured within the folded portion, the longitudinally-extending absorbent composite comprising a first cuff fabric, a second cuff fabric bonded to the first cuff fabric, and particles adhered between the first and second fabric. The longitudinally extending absorbent composite may be sections of one continuous absorbent composite. The top sheet may be comprised of the first fabric of the absorbent composite. The absorbent core may comprise the absorbent composite. The absorbent composite of the core may further comprise particles positioned on the second fabric, and a third fabric bonded to the second fabric. The absorbent composite of the core may further comprises a third fabric positioned adjacent to the second fabric, a fourth fabric bonded to the third fabric, and particles adhered between the third and fourth fabrics. The second and third fabrics may be unitary.

The novel article may include a backsheet and a core that is comprised of the absorbent composite. The article may further include an acquisition layer positioned relative to the absorbent core. The article may also include a topsheet that is comprised of the first fabric.

An alternative embodiment of the novel absorbent article comprises a topsheet, a backsheet, an absorbent composite comprising a first fabric, a second fabric bonded to the first fabric, and an absorbent layer of particles adhered between the first and second fabric, wherein the absorbent layer is disposed between the topsheet and backsheet, and generally centrally at a location identified as a crotch region, the absorbent layer" providing an absorbent core for absorbing bodily exudates received in the crotch region.

The alternative embodiment may further comprise a pair of longitudinally-extending, upstanding cuffs spaced laterally from the absorbent core, each the cuff including a folded portion of the topsheet and a longitudinally-extending absorbent composite secured within the folded portion, the longitudinally-extending absorbent composite including a first cuff fabric, a second cuff fabric bonded to the first cuff fabric, and an absorbent layer of particles adhered between the first and second cuff fabric. Additionally, the absorbent composite located at the crotch region and the longitudinally extending absorbent composites of the cuffs may be sections of one continuous absorbent composite structure positioned about the crotch region.

The alternative embodiment may include an absorbent layer that is supported on the backsheet, such that a section of the backsheet provides the second fabric of the absorbent composite. The backsheet may further comprises a first backsheet layer, a second backsheet layer and SAP particles in a concentration of about 20 gsm positioned there between and the second back sheet layer is an SMS having a basis weight in the range of about 10 gsm to 60 gsm. The absorbent layer may be adhered between the first and second fabric with an adhesive concentration of between 1 and 100 grams per square meter. The first fabric may be bonded to the second fabric at discrete points, which discrete points may define pockets. Further, the first fabric may be bonded to the second fabric along a plurality of bond lines, which bond lines may define pockets.

In still another alternative embodiment, the novel absorbent articles comprise a topsheet, a backsheet, and an absorbent core disposed between the topsheet and the backsheet, the absorbent core comprising, a first fabric, a second fabric, bond sites at which the first fabric is connected to the second fabric; and an absorbent layer of particles adhered between the first and second fabric. The particles may be SAP particles and/or other beneficial particles. The absorbent layer may be supported underneath a section of the topsheet, such that the section of topsheet provides the second fabric of the absorbent composite. The absorbent layer may be supported on a section of the backsheet, such that the backsheet section provides the first fabric of the absorbent composite.

The still another embodiment of the novel disposable absorbent article may include a concentration of SAP particles in the absorbent layer of between about 50 and 650 grams per square meter. The SAP particles may also be coated with a hydrophobic material to retard the initial receipt of liquid by the SAP particles in the absorbent layer. The bond sites may define a plurality of continuous lines that inhibit the movement of the SAP particles of the absorbent layer. The continuous lines may be shaped to form pockets between the first and second fabrics. The bond sites may define a plurality of discontinuous lines that inhibit the movement of the SAP particles of the absorbent layer. The discontinuous lines may be shaped to form pockets between the first and second fabric.

In yet another embodiment, the novel absorbent composite comprises a first fabric, a second fabric bonded to the first fabric, and an effective concentration of particles secured between the first and second fabric. The effective concentration of particles may be secured using adhesive, thermal plastic or a combination thereof. The first fabric may be bonded to the second fabric using either thermal or ultrasonic bonds. The adhesive may be applied to the first and second fabric. The adhesive may be applied in a concentration of between 1 and 100 grams per square meter.

In the yet another embodiment, the bonds may be positioned along periphery of pockets of particles. The bonds may form a pattern such as herringbone, bricklayer, circles, triangles, dots, dashes, rectangles, and combinations thereof. The yet another embodiment may also include loose particles positioned between the first and second sheets.

The foregoing has outlined rather broadly the features and technical advantages of the present invention in order that the detailed description of the invention that follows may be better understood. Additional features and advantages of the invention will be described hereinafter. It should be appreciated that the specific embodiments disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Upon review of the detailed description and the accompanying drawings provided herein, it will be apparent to one of ordinary skill in the art that an absorbent composite made according to the present invention may be used in disposable absorbent articles, and more particularly, in disposable absorbent articles, such as diapers, training pants or other incontinence products. Accordingly, the present invention shall not be limited to the structures and processes specifically described and illustrated herein, although the following description is particularly directed to an absorbent composite that is used in a disposable diaper. The term "absorbent article" or "absorbent garment" with which the present invention is associated, includes various types of disposable articles and garments which are placed against or in proximity to the body of the wearer so as to absorb and contain various bodily exudates, bodily fluid, or biofluid.

Figure 1:
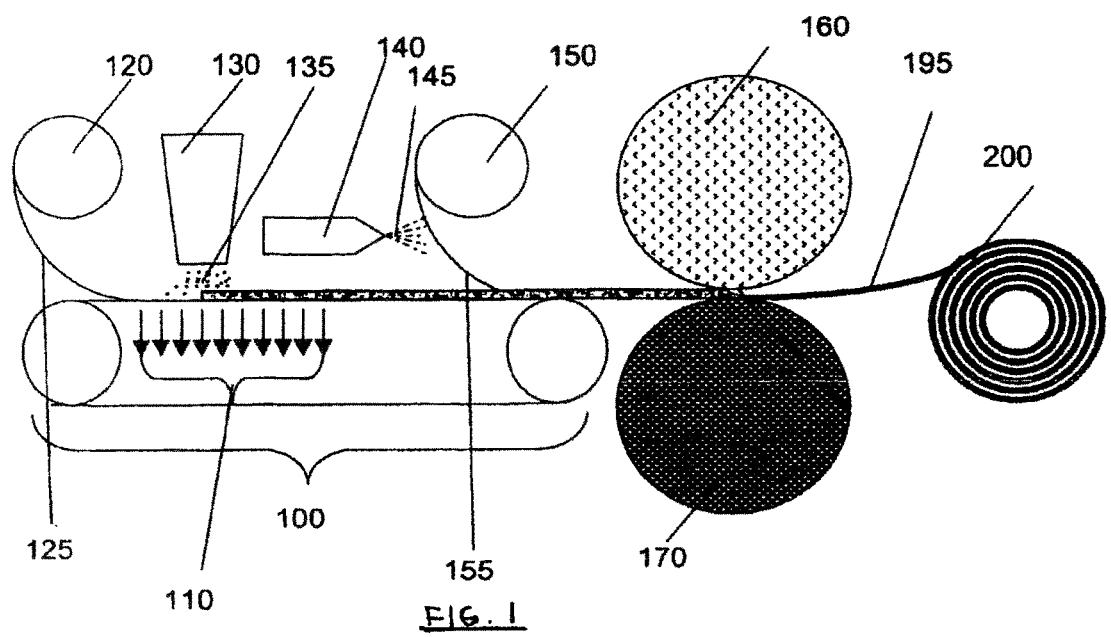
FIG. 1 is a schematic of one embodiment of a method of making the inventive absorbent composite using calendar rolls.

Turning now to the figures, FIG. 1 shows one embodiment of the inventive method. In FIG. 1, a fabric 125 is shown as it is dispensed from roll 120 and carried along a production line on a conveyer belt 100. According to one embodiment, the fabric 125 is a thermal plastic material that may be a woven, nonwoven, film, or a combination thereof. The fabric 125 is secured to the conveyer belt 100 by a vacuum system 110. The vacuum system 110 serves to confirm the fabric 125 to the convey belt 100.

In one embodiment, the surface of the conveyor belt 100 has recessed portions that form cups in the fabric 125 as the fabric is pulled against the surface of the conveyor belt 100. The surface of the conveyor belt 100 is not limited to constructions that form cups in the fabric but, instead, may be configured with a number of different surface shapes and sizes. Examples include ridges, raised shapes, and holes. In addition, the surface shapes may be distributed uniformly or non-uniformly across the width and length of the conveyor belt. Alternatively, the conveyor belt 100 may be flat. In applications in which the conveyor belt 100 has holes or other similar constructions, the depth of the pockets formed in the fabric 125 may be varied by the force of the vacuum system 110, the elasticity of the fabric 125, or a combination thereof. Additionally, heat may be used to increase the elasticity of the fabric 125 as the fabric is pulled against the surface of the conveyor belt 100. Heat may be applied to the fabric by way of a heated conveyor belt or any other means known in the art. The vacuum 110 may be applied uniformly across the surface of the conveyor belt 100 or at selected locations. For example, in a configuration in which the surface of conveyor belt 100 has depressions, vacuum may be applied only at the depressions.

The SAP particles 135 are then deposited on the fabric 125 by a SAP dispenser 130. The SAP dispenser 130 may be configured to position SAP particles in their desired position on the first fabric or may be configured merely to deposit SAP particles on the first fabric, wherein the SAP particles are position by another means. One skilled the art understands that multiple SAP dispensers 130 may be used. The SAP particles 135 may be deposited, positioned, or both on the fabric 125 by wind or other known methods. Alternatively, the conveyor belt shown in FIG. 1 may be inverted so that the vacuum system 110 applies suction from above. In such a configuration, the fabric 125 is carried over a supply of SAP particles 135 and the SAP particles are held onto the surface of fabric 125 by vacuum system 110. In an alternative embodiment, SAP dispenser 130 may include skin care particles such as ion exchange resins, deodorant, anti-microbial agents, binder particles, or other beneficial particles. Further, although the preferred embodiment is directed to SAP particles, the methods disclosed herein can be used with any combination of the above referenced particles, including combinations that do not include SAP. Alternatively, a separate dispenser advantageously positioned along the production line (not shown) may be used to deposit different types of particles such as, for example, skin care particles.

The SAP particles 135 are positioned and concentrated on the fabric 125 according to a number of alternative methods. In one embodiment, the vacuum system 110 and fabric 125 may be configured to allow the vacuum system 110 to pull the SAP particles 135 against the surface of the fabric 125 uniformly or in particular areas. In another embodiment, the shape of the fabric 125 guides the SAP particles 135 into position. For example, when the fabric 125 is shaped to form pockets, the SAP particles 135 roll into the pockets as a result of the vacuum system 110, the vibration of the conveyor belt, wind, the angle of the conveyor belt, or combinations thereof. Alternatively, the SAP dispenser(s) 130 may be positioned and controlled to dispense SAP particles 135 strategically across the surface of fabric 125, which strategic positioning includes but is not limited to alignment or nonalignment with the machine direction, offset, or randomly. Further, SAP may be positioned such that there are zones without SAP particles. Still further, SAP particles may be positioned using adhesive such as by applying adhesive to specific locations on a surface, depositing SAP particles on the surface. Still further, SAP particles may be positioned on both fabrics 125 and 155.

Once SAP particles have been deposited and positioned on fabric 125, a second fabric 155 is introduced into the production line from roll 150. The second fabric 155 may be selected from a variety of materials including spun-bonded thermoplastic or similar woven or nonwoven material, film, or combinations thereof.

The adhesive 145 is applied to the SAP particles 135 in a number of ways. FIG. 1 shows the adhesive 145 applied to the fabric 155. Alternatively, the adhesive 145 may be applied to the fabric 125 and SAP particles 135, fabric 125 before the SAP particles 135 are deposited on the fabric 125, or directly to the SAP particles before they are deposited on the fabric 125. In still another embodiment, the adhesive 145 is applied at the point where fabrics 125 and 155 are jointed together. In still another embodiment, multiple coats of adhesive are applied. For example, adhesive 145 may be applied to the fabric 125 before the SAP particles 135 are deposited, to the SAP particles 135 after they have been positioned, to the fabric 155, or a combination thereof. Alternatively or in addition to the above embodiments, binder particles may be mixed with the SAP particles 135. Additionally, the adhesive may be applied uniformly, randomly, or in a specific pattern, depending the desired absorbent properties of the finished composite.

The adhesive is applied according to a number of methods know to those skilled in the art. For example, the adhesive may be sprayed, rolled, or spun onto the surface of fabric 155. The adhesive may be hydrophobic, hydrophilic, biodegradable, bioderived, or combinations thereof. The preferred adhesive is hydrophobic. The concentration of adhesive in a coat varies between 1 and 100 grams per square meter ("GSM"). Optimally, the concentration is between 5 and 75 GSM. In a preferred embodiment, the concentration is between 12 and 50 GSM. Additionally, enough adhesive should be applied to cover at least 25% of the targeted area.

Fabrics 125 and 155 are then bonded together. FIG. 1 shows a thermal bonding system in which calendar rolls 160 and 170 are used. However, other bonding systems/methods may be used. For example, the ultrasonic bonding system of FIGS. 4 and 5 may be used. Adhesive 145 retains the SAP particles 135 in a relatively fixed position with respect to the fabrics during the bonding process and subsequent to the bonding process. The bond pattern may be aligned with the distribution of the SAP particles 135. Alternatively, the bond pattern may not be aligned with the distribution of the SAP particles 135. In such embodiments, the bonding equipment may be adapted to nudge the SAP particles 135 aside prior to bonding or to bond through the SAP particles 135. These embodiments eliminate the need to synchronize the pend-bond points with the distribution of SAP particles.

Fabrics 155 and 125 are shown as two materials. However, one skilled in the art understands that the fabrics may actually be part of the same material. In such a configuration, the unitary fabric is folded to cover the SAP particles. Alternatively, the edges of fabric 125 may be folded prior to applying the second fabric 155. In embodiments in which fabrics 125 and 155 are separate, fabrics 125 and 155 may be the same or a different material. Additionally, fabric 155 may be sized to cover specific areas, such as the center section, of fabric 125.

Once the fabrics have been bonded together, the absorbent composite 195 is collected on rewinder 200.

Figure 2:
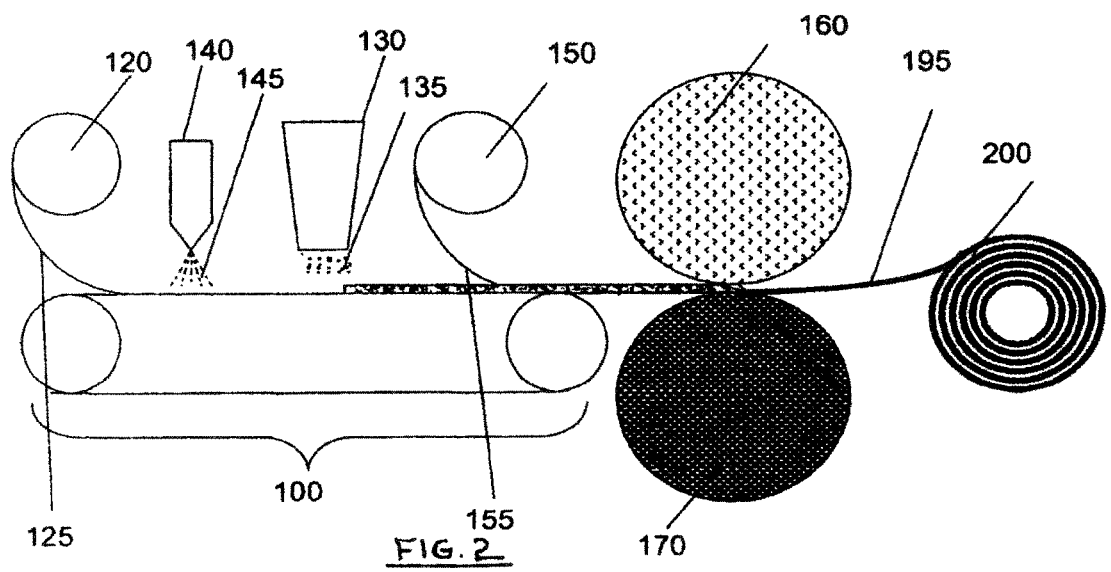
FIG. 2 is a schematic of another embodiment of a method of making the inventive absorbent composite using calendar rolls.

FIG. 2 shows the preferred embodiment of the inventive method. The fabric 125 is transported along the conveyor belt 100. As fabric 125 is transported along the conveyor belt 100, a thin coat of adhesive 145 is applied to fabric 125. As with the method of FIG. 1, the adhesive may be applied uniformly, randomly, or in a specific pattern, depending the desired absorbent properties of the finished composite. Although the adhesive 145 is shown being applied before the SAP Particles 135 are deposited, alternate embodiments are envisioned. For example, the adhesive may be applied according to the embodiments described with respect to FIG. 1.

Following the application of the adhesive, SAP particles 135 are deposited and positioned on the fabric 125. The SAP particles 135 may be deposited directly on fabric 125, as shown in FIG. 2, or indirectly, such as by wind blowing SAP particles across fabric 125. The weight of the SAP particles aids in securing the fabric 125 to the conveyor belt 100. Additionally, the SAP particles may be positioned in a manner similar to that disclosed for FIG. 1.

A second fabric 155 is then fed into the production line from roll 150. The second fabric is positioned to cover the SAP particles 135. The adhesive 145 prevents the SAP particles from moving freely between the two fabrics. The resulting sandwiched construction is then transported to the calendar rolls for thermal bonding. As described with respect to FIG. 1, the bond pattern may be aligned or not aligned with the SAP particles 135. The absorbent composite 195 is then collected by rewinder 200. As described with respect to FIG. 1, fabrics 125 and 155 may be part of a single sheet. Additionally, the fabrics may be folded in the manner described for FIG. 1. In another embodiment, the fabric 125 may be coated with adhesive and pressed on a supply of SAP particles.

Figure 3:
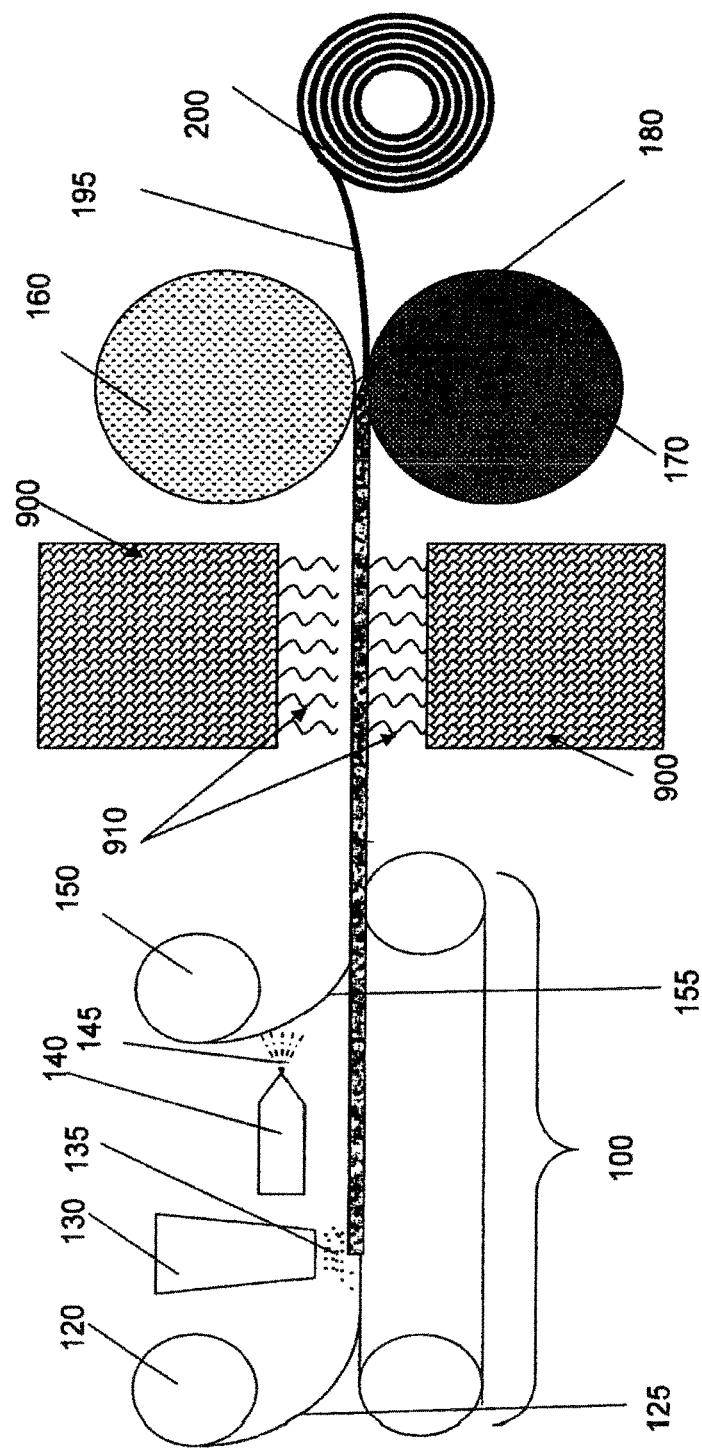
FIG. 3 is a schematic of the inventive method shown in FIG. 1 with an additional energy source.

FIG. 3 is similar to FIGS. 1 and 2, except that an energy source 900 such as an oven or microwave generator is positioned along the assembly line. The energy source applies heat and or radiation 910 that can be used to melt thermal plastic binder. The amount of heat may also be regulated to melt specific types of particles or fibers, specific sections of the fabrics, or only the outer layers of particles/binder.

Figure 4:
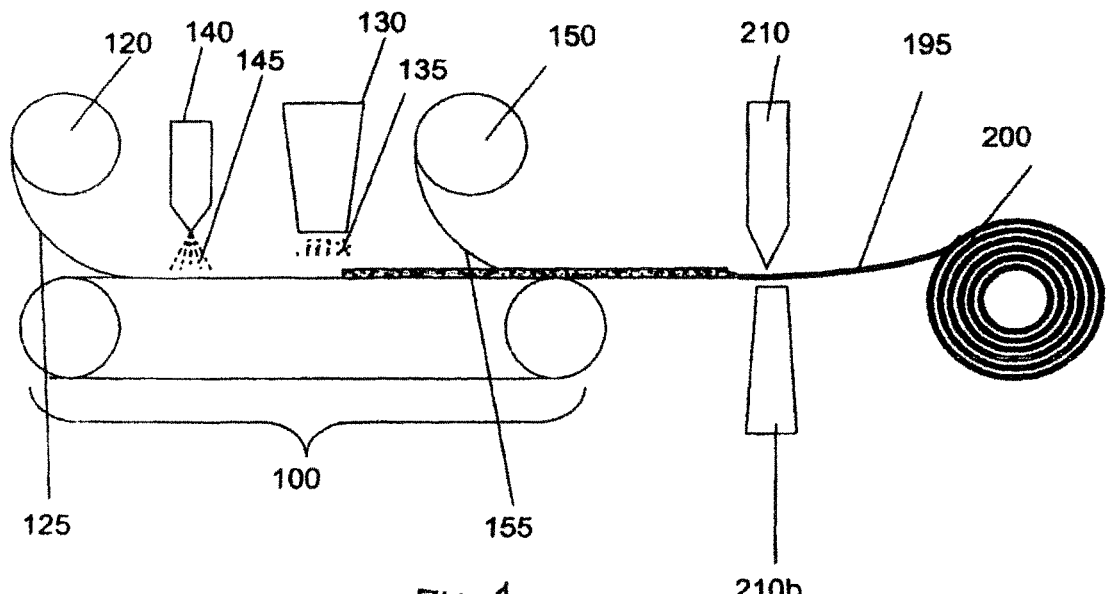
FIG. 4 is a variation of the method shown in FIG. 1 that uses ultrasonic bonding techniques instead of calendar rolls.
Figure 5:
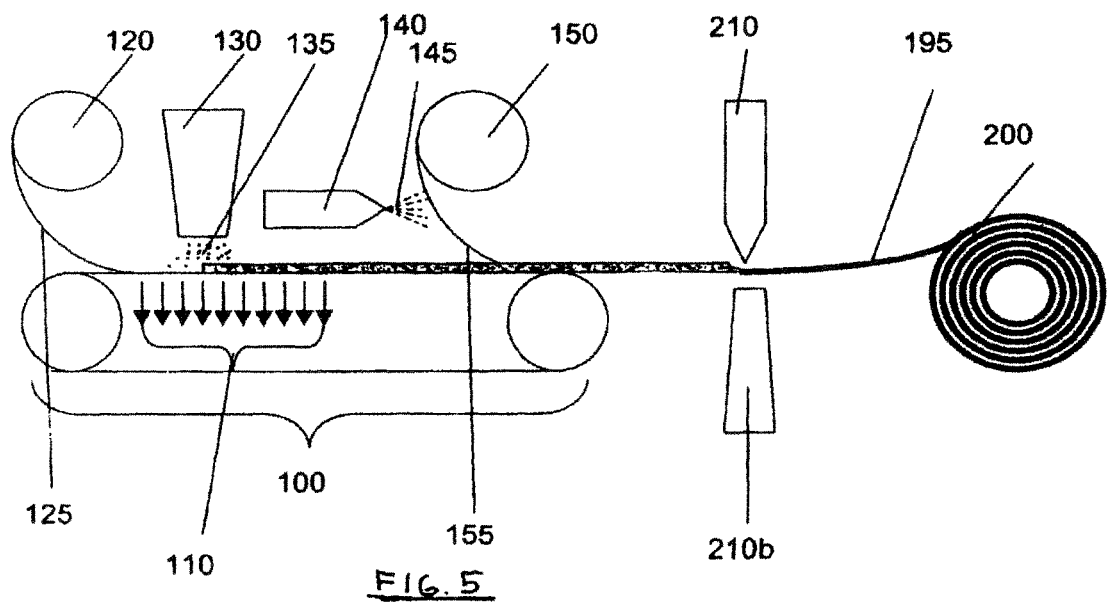
FIG. 5 is a variation of the method shown in FIG. 2 that uses ultrasonic bonding techniques instead of calendar rolls.

FIGS. 4 and 5 are similar to FIGS. 1 and 2, except that the fabrics are bonded together using ultrasonic bonds. FIGS. 4 and 5 show an ultrasonic bonding system (210a and 210b). It is readily understood that FIGS. 1-5 show different embodiments of the novel method and that aspects of the various methods may be advantageously combined depending on the need. Important to all combinations, however, is the amount of adhesive 145, binder particles, or combinations thereof applied to the SAP particles 135 and the strength of the bonds. As noted with respect to FIG. 1, the optimal concentration of adhesive is between 12 and 50 GSM, though other concentrations are acceptable. In all embodiments, it is important that the concentration of adhesive 145 be high enough to inhibit the migration of SAP particles 135. The concentration should not be so high, however, that it coats the SAP particles 135 and reduces SAP swelling. The adhesive should only inhibits the migration of enough SAP particles 135 to assure uniform absorbency. Although not shown, one skilled in the art understands that the energy source 900 shown in FIG. 3 can also be applied in the configurations shown in FIGS. 2, 4 and 5.

Figure 6:
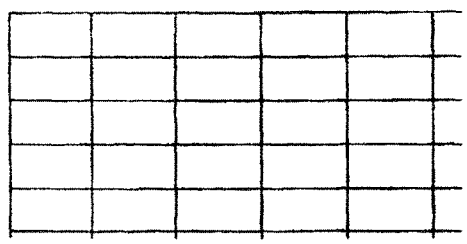
FIG. 6 is an illustration of various potential bonding patterns that may be used in the inventive method and absorbent article.
Figure 6:
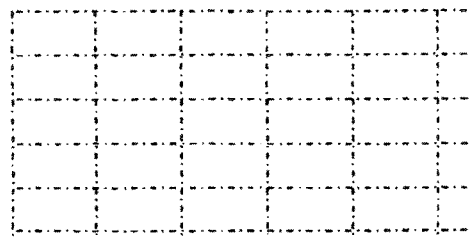
Figure 6:
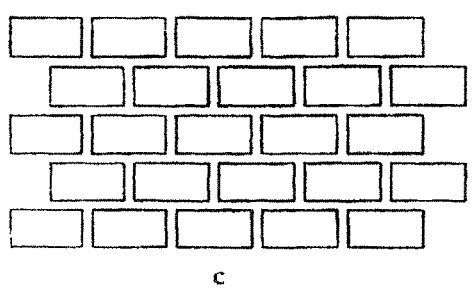
Figure 6:
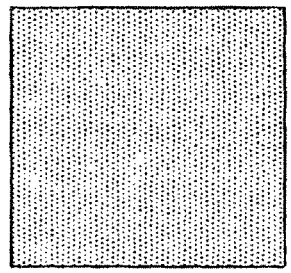
Figure 6:
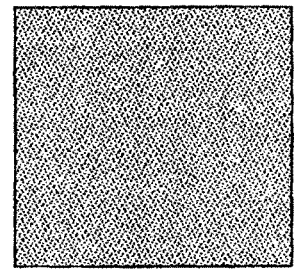
Figure 6:
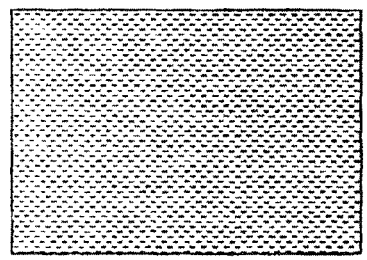
Figure 6:
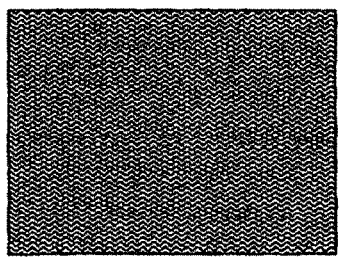
Figure 6:
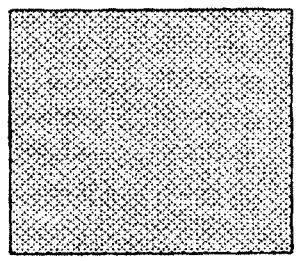
Figure 6:
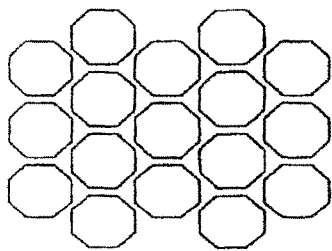
Figure 6:
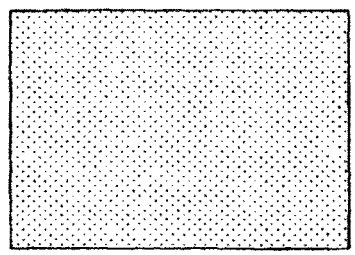
Figure 6:
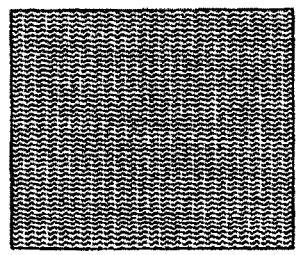
Figure 6:
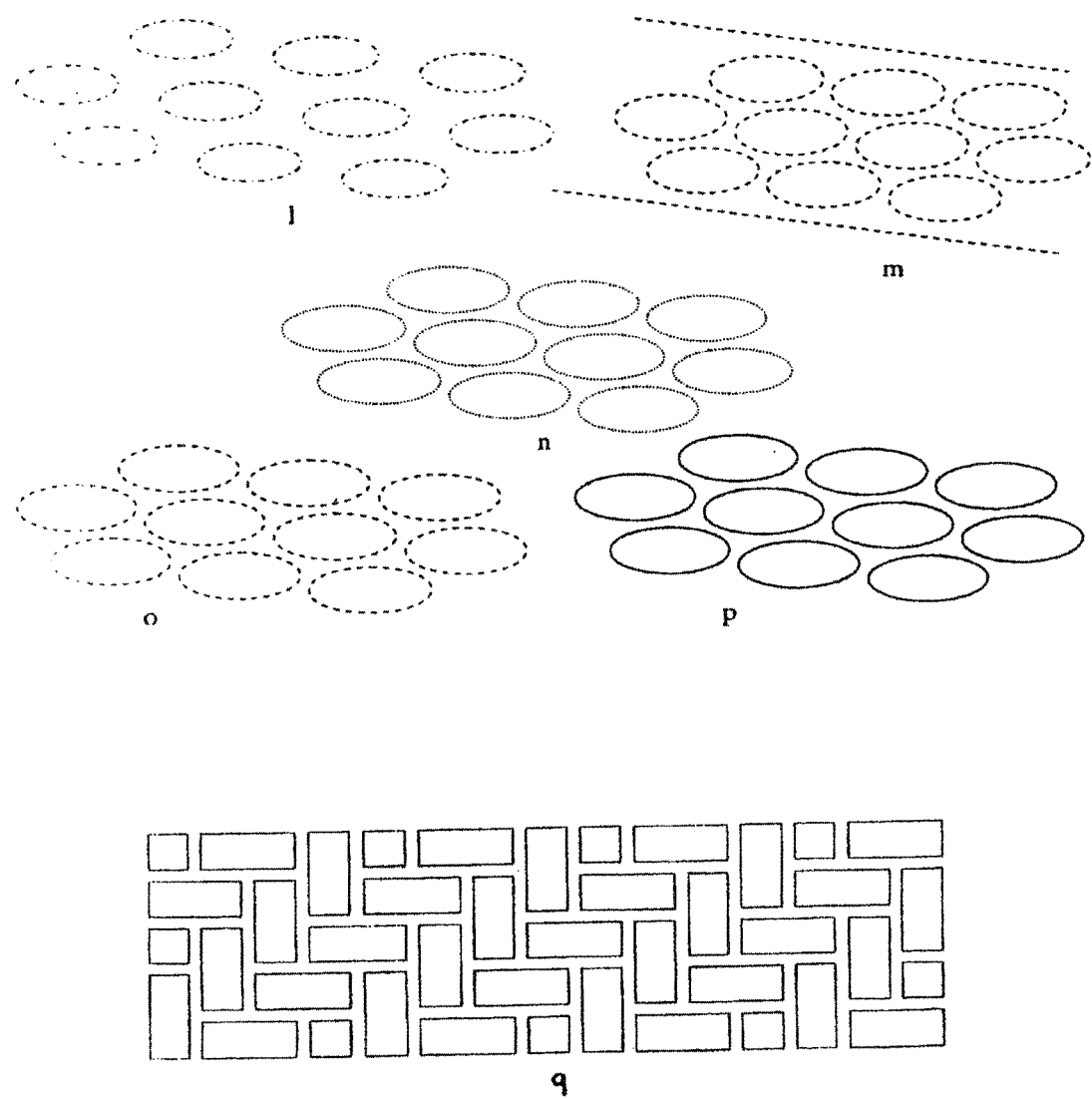

FIG. 6(a) through (q) show various bonding patterns contemplated by the inventive method. The bonding patterns may completely enclose an area, partially enclose an area, or provide local bonding zones. The lines and points indicate the bond sites. The solid lines depict bond lines. The bond lines may form open shapes or enclosed shapes, such as can be found in examples (a) and (c), which depict continuous bond lines that completely enclose pockets of SAP particles 135 or, as in example (g), separate distinct regions of the absorbent composite. The dashed lines, such as can be found in examples (b) and (m), are discontinuous bond patterns that do not completely enclose pockets of SAP particles 135. In these configurations, the migration of dry SAP particles is inhibited by the adhesive and continuous or discontinuous bond patterns. Discontinuous bond patterns may be substituted for continuous bond patterns and visa versa. Further, though the FIG. 6 shows either continuous or discontinuous bond patterns, combinations of discontinuous and continuous bond patterns may be used.

Figure 7:
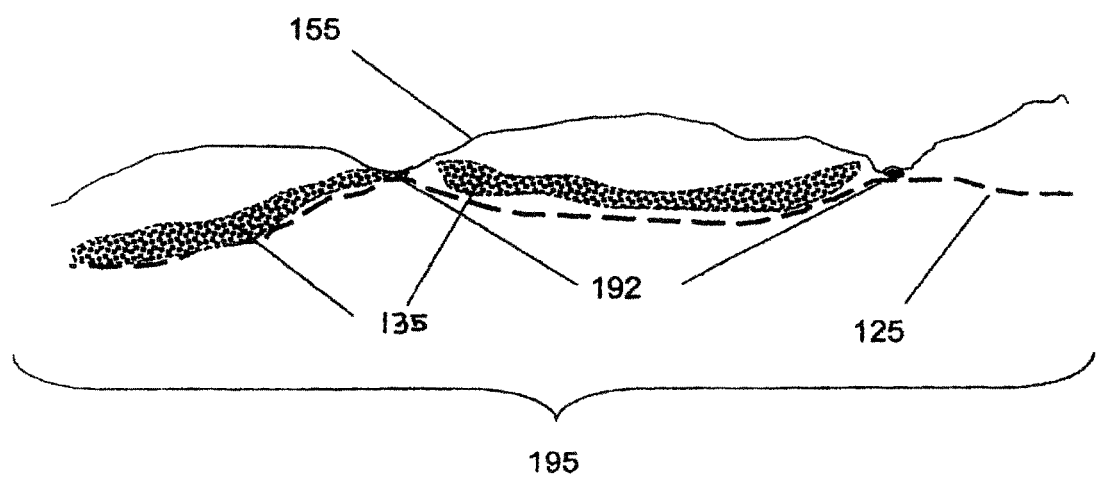
FIG. 7 is a cross sectional illustration of a pockets formed by the inventive method and utilized in the inventive absorbent article.

FIG. 7 shows a partial cross-section of an absorbent composite 195. FIG. 7 shows how bonds 192 may act to separate pockets of SAP particles 135. As noted with respect to the bonding pattern, SAP particles 135 may be entirely enclosed in pockets defined by the bonding pattern, partially enclosed in pockets defined by the bonding pattern or merely inhibited by the bonding pattern. Inhibited in this context means the SAP particles 135 cannot move directly from one area of the core to another area, but instead, must move around bond sites.

In one aspect of the invention, multiple functions or advantageous properties are obtained in the absorbent composite by varying the amount of SAP particles, the type and number of fabrics used, and construction variables such as, the ratio of SAP to adhesive, and applying the absorbent composite at various locations in the article.

Additionally, one skilled in the art understands that the process for constructing a single absorbent composite described above may be modified to produce a multiple, laminated absorbent composite. In structures comprising multiple layers, the layers may be sheets of absorbent composite 195 that are laminated together to form a single structure or alternating layers of fabric and SAP particles 135 that form a single structure. One skilled in the art understands that alternating layers may be achieved by applying adhesive to the top of fabric 155 (FIG. 1), applying a second layer of SAP particles 135, and a third fabric (not shown). Similarly, additionally layers may be added, limited only by the maximum thickness suitable for the bonding process.

In anyone of the embodiments of the absorbent composite, the SAP particles 135 may be coated with a miscible, hydrophobic material. The coating acts as a barrier or membrane that initially slows the liquid uptake, thereby saving SAP capacity for additional or secondary discharges. In this regard, the coating evens out the absorbency rates between discharges. In the processes shown in FIGS. 1 to 5, the coating may be applied prior to the adhesive 145 being applied, after the adhesive 145 is applied, or at the same time. Alternatively, the adhesive may be mixed with the coating material.

In one embodiment, a light coating of mineral oil is applied over the SAP particles 135. The coating retards the initial uptake by the SAP particles and allows more time for the liquid to spread out in the article. Preferably, the mineral oil is applied at a concentration of about 0.00001 grams per gram of SAP to about 0.1 grams per gram of SAP (depending on the particular product design). Alternatively, the mineral oil may be applied in specific target zones. In this way, the received liquid is encouraged to initially spread to uncoated areas before the coated areas are activated and begin to swell.

An absorbent composite manufactured by the above-described process may be used for a disposable absorbent article or as one or more of the components of a disposable absorbent article. The components of an absorbent article include the backsheet, topsheet, absorbent core, containment walls or cuffs (including leg gathers), backsheet/absorbent core composite, topsheet/absorbent composite, and combinations thereof. Such constructions are described below in more detail.

Figure 8:
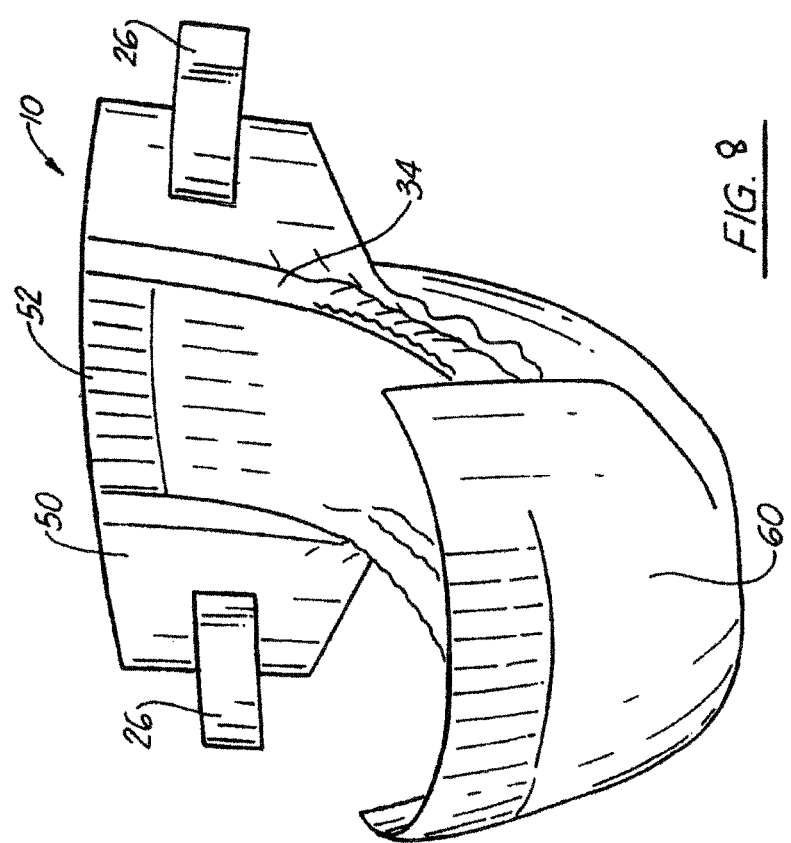
FIG. 8 is a perspective view of a disposable absorbent article embodying the inventive absorbent composite.

FIG. 8 is a perspective view of one embodiment of a disposable absorbent article m the form of a diaper 10. Diaper 10 comprises a topsheet 50, a backsheet 60, and an absorbent core (not shown). The diaper further comprises upstanding barrier cuffs 34 which extend longitudinally along the diaper and are elasticized to conform to the buttocks of the wearer. Additionally, the diaper includes an elastic band 52 and fastening elements 26. Element 26, in use, extends to and engages the corresponding opposing end of the diaper to secure the diaper about the wearer.

Figure 9:
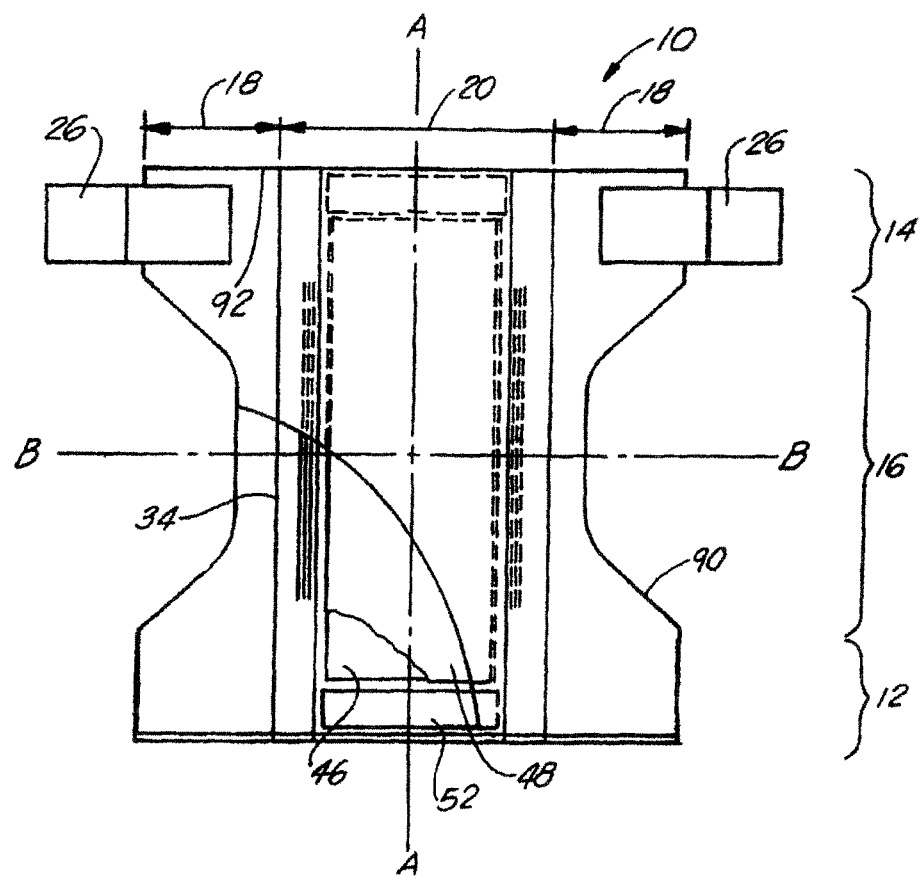
FIG. 9 is a top plan view of the disposable absorbent article of FIG. 8 in a flat and extended condition.

FIG. 9 illustrates a composite web structure of the diaper 10 of FIG. 8 in a generally flat and unfolded configuration. As will be explained further below, the web structure may be subsequently trimmed, folded, sealed, welded and/or otherwise manipulated to form a disposable diaper 10 in a finished or final form. To facilitate description of the diaper 10 embodying the invention, the description refers to a longitudinally extending axis AA, a laterally extending central axis BB, a pair of longitudinally extending side edges 90, and a pair of end edges 92 which extend between side edges 90. Along the longitudinal axis AA, the diaper 10 includes a first end region or front waist region 12, a second end region or back waist region 14, and a crotch region 16 disposed therebetween. Each of the front and back waist regions 12, 14 is characterized by a pair of ear regions or ears 18, which are located on either side of a central body portion 20 and extend laterally from the side edges 90. A fastening structure 26 (e.g., a conventional tape fastener) is affixed to each of the ears 18 along the back waist region 14 of diaper 10.

When the diaper 10 is worn about the waist, the front waist region 12 is fitted adjacent the front waist area of the wearer, the back waist region 14 is fitted adjacent the back waist area, and the crotch region 16 fits about and underneath the crotch area. To properly secure the diaper 10 to the wearer, the ears 18 of the back waist region 14 are brought around the waist of the wearer and toward the front and into alignment with the ears 18 of the front waist region 12. The securing surface may be located on or provided by the interior or exterior surface of the front waist region 12. Alternatively, the fasteners 26 may be located on the ears 18 of the front waist region 12 and made securable to the ears 18 of the back waist region 14.

Figure 10:
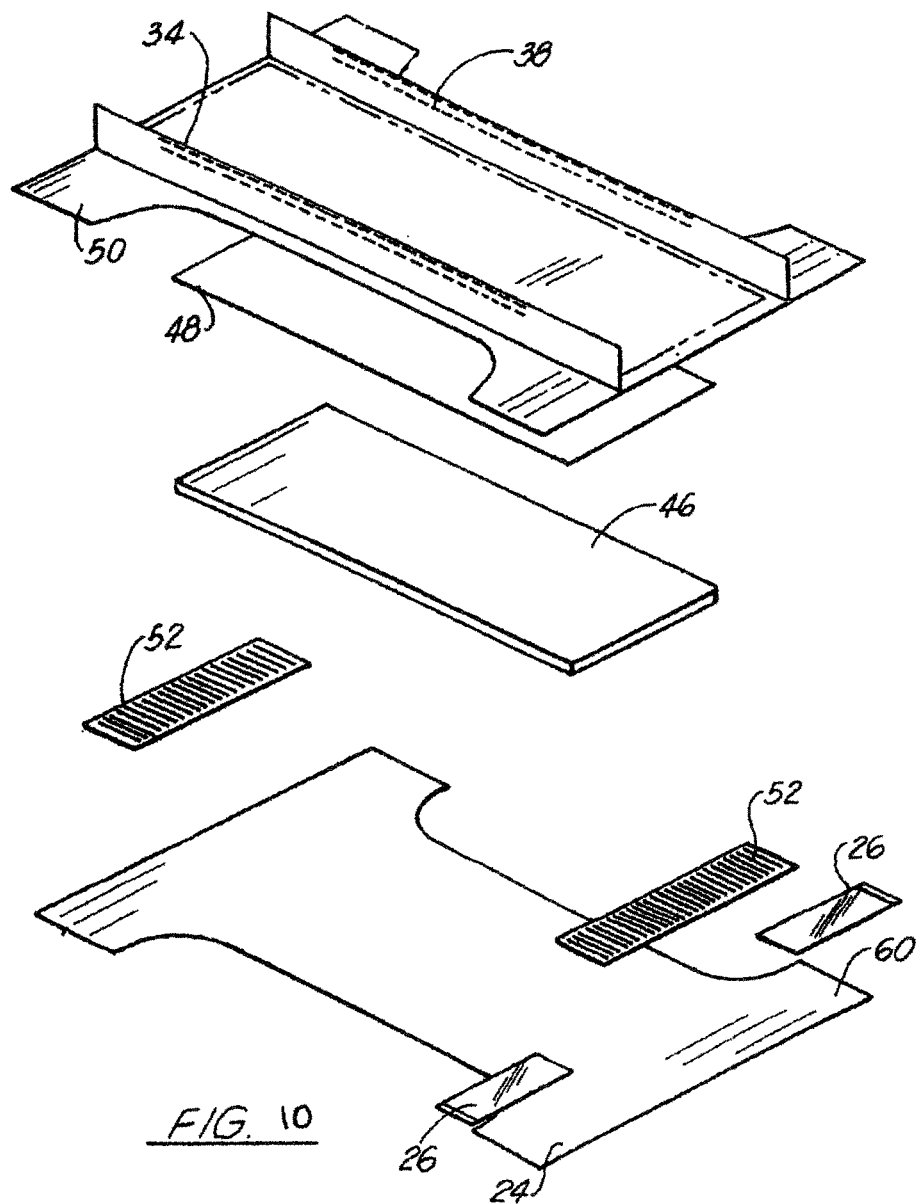
FIG. 10 is an exploded view of the disposable article of FIG. 8.

FIG. 10 is an exploded view of the diaper of FIGS. 8 and 9. A diaper structure suitable for the present invention typically employs at least three layers. These three layers include a backsheet 60, an absorbent core 46, and a topsheet 50. The diaper structure mayor may not contain a pair of containment walls or leg cuffs 34 disposed upwardly from the topsheet 50 and preferably equipped at least with one or more spaced apart, longitudinally elastic members 38. It will be shown below that any of these diaper elements or a combination of these elements may be constructed with or using the absorbent composite 195. Additionally, an acquisition layer 48 could be added to improve performance.

Backsheet

As mentioned above, the diaper 10 employs a backsheet 60 that covers the core 46 and preferably extends beyond the core 46 toward the side edges 90 and end edges 92 of the diaper 10. In one aspect of the invention, the backsheet 60 is constructed from a single-layered material sheet of absorbent composite 195. In such a configuration, fabric 125 is positioned as an outer surface of the backsheet 60.

Additionally, an alternative embodiment could be used for gel blocking. For an application using gel blocking, a backsheet of the inventive disposable absorbent article is relatively thin and provides improved flexibility. When dry, the backsheet is soft and breathable, but upon wetting, a thin, gel blocked layer is formed (i.e., on the inner surface of the backsheet) which renders the backsheet substantially liquid impervious. The gel blocked layer is formed by the swelling of the SAP particles 135.

Topsheet

Similarly, the inventive absorbent composite 195 may be utilized with or as the topsheet of an absorbent garment. The topsheet 50 is preferably soft, compliant, exhibits good strikethrough and a reduced tendency to rewet from a liquid pervious material. The topsheet 50 is placed in close proximity to the skin of the wearer when the diaper 10 is worn. In this way, such a topsheet 50 permits bodily discharges to rapidly penetrate it so as to flow toward the core 46 more quickly, but not allowing such discharges to flow back through the topsheet 50. The topsheet 50 may be constructed from anyone of a wide range of liquid and vapor permeable hydrophilic materials. The surface(s) of the topsheet may be treated with a surfactant so as to facilitate liquid transfer therethrough, especially at a central zone or area of the topsheet located over the core and an inner surface of the core. The topsheet may also be coated with a substance having rash preventing or rash reducing properties (e.g., aloe vera).

In one embodiment, the topsheet 50 is formed from an absorbent composite 195 that covers substantially the entire area of the disposal absorbent article 10, including substantially all of the front waist region 12, back waist region 14, and crotch region 16. Further, the ear layer of the inner region 18 is formed from the same single topsheet material and, thus, may be referred to as being unitary with the topsheet 50 in forming lateral extensions of the topsheet material. Alternatively, the topsheet 50 may be formed from multiple different materials which vary across the width of the topsheet 50. Such a multiple piece design allows for creation of preferred properties and different zones of the topsheet.

Absorbent Core

Figure 11:
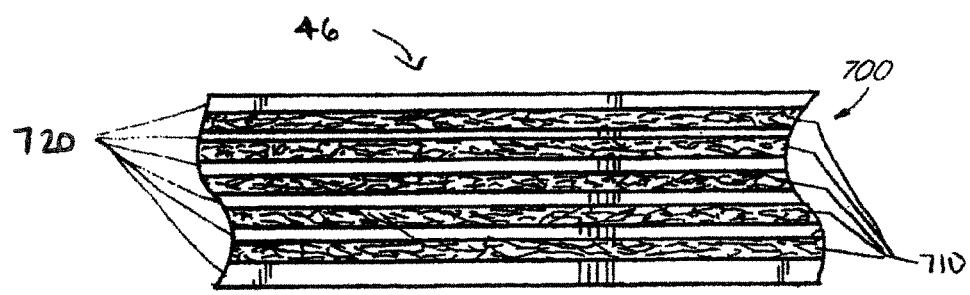
FIG. 11 is a partial cross-sectional view of an absorbent core utilizing the inventive absorbent composite and employed by an absorbent article according to the present invention.
Figure 12:
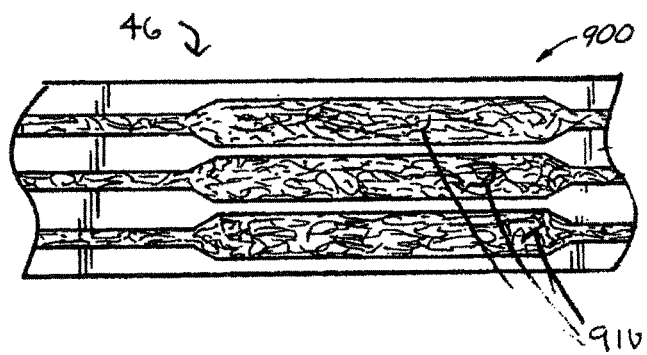
FIG. 12 is partial cross-sectional view of an absorbent core utilizing an alternative embodiment of the inventive absorbent composite and employed by an alternative absorbent article according to the present invention.

In addition to or as an alternative to the above embodiments, the absorbent core of the disposable absorbent article may be constructed from the absorbent composite 195, laminated layers of absorbent composite 195 (not shown) or multiple layers of SAP particles 135 and fabric. FIGS. 11 and 12 depict cross sectional views of alternating layers of SAP particles 135 and fabric that form a multi layered absorbent composite 700 and 900, respectively. As shown in these drawings, the core 46 may be comprised of distinct layers of SAP particles 135 (710 and 910). The layers may be uniform or non-uniform, depending on the intended application. In the non-uniform multi layered absorbent composite 900, the concentration of SAP particles 135 may vary within a given layer, between layers, or combinations thereof.

FIG. 11 depicts a composite structure 700 in which SAP particle layers 710 and fabric layers 720 are alternated to form the completed composite structure 700. The layered design can also be constructed by bonding together sheets of absorbent composite, folding a unitary sheet of absorbent composite, or constructing absorbent composites with multiple layers during the manufacturing process. In folded applications, the composite fold may be a C-fold, Z-fold, V-fold, W-fold or combinations thereof. Further, the folds may be open, closed, or overlapping.

FIG. 12 depicts multi layers absorbent composite 900. As shown in FIG. 12, high concentrations areas of SAP particles 910 may be strategically positioned to provide additional absorbency in specific regions such as the crotch of an absorbent article. One skilled in the art understands that the high concentration areas may be offset to control the amount and direction of liquid penetration. Additionally, the layer with zones of high concentrations may be combined with layers of substantially uniform layers. Alternatively, the high SAP concentration areas can be formed by positioning multiple layers of absorbent core.

The core according to various embodiments of the invention may be configured to extend substantially the full length and/or width of the disposable absorbent article. Preferably, however, the core is disposed or is otherwise concentrated at the crotch region of the article. In various embodiments, the core extends to the edges of the article and the SAP particles 135 are concentrated in the crotch region or another target zone of the article. In still another embodiment, the particles can be a combination of SAP particles, skin care particles such as ion exchange resins, deodorant, anti-microbial agents, binder particles, or other beneficial particles.

Containment Walls

Figure 13:
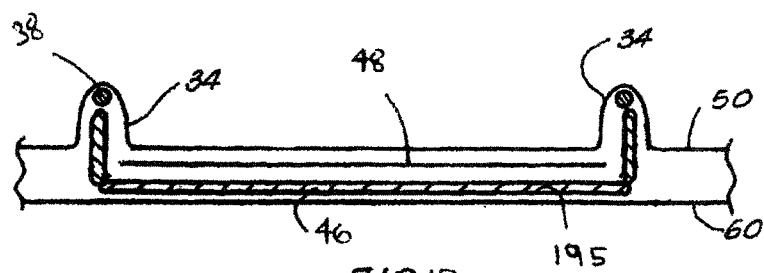
FIG. 13 is a cross-sectional view of an absorbent article employing in the leg cuffs an absorbent composite according to the present invention.
Figure 14:
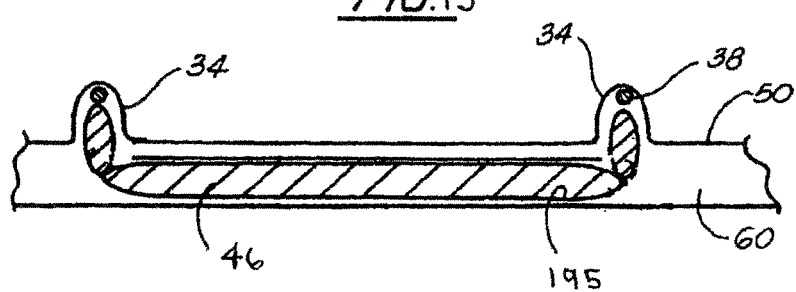
FIG. 14 is a cross-sectional view of an absorbent article employing in the leg cuffs a saturated absorbent composite according to the present invention.

Now turning to FIGS. 13 and 14, in yet another aspect of the invention, the inventive disposable absorbent article 10 utilizes a pair of containment walls or cuffs 34 which employ the absorbent composite 195. Each containment wall 34 is a longitudinally extending wall structure preferably positioned on each side of the core 46 and spaced laterally from the longitudinal center. The longitudinal ends of the walls 34 may be attached, for example, to the topsheet 50 in the front and rear waist regions 12 and 14. Preferably, the ends of the containment wall 34 are tacked down inwardly and attached, for example, by adhesive to the web structure. Such a construction effectively biases the containment wall 34 inwardly and is generally considered to cause containment wall 34 to exhibit improved leakage prevention properties.

FIG. 13 provides a cross-sectional view of a diaper 10 according to the invention. The diaper 10 includes backsheet 60, absorbent core 46, acquisition layer 48, and topsheet 50. As shown in FIG. 13, the core is an absorbent composite 195. The diaper 10 also includes a pair of containment walls or cuffs 34 which are formed by folding the topsheet 50 and wrapping it about the ends of the absorbent composite 195. Alternatively, the absorbent composite 195 in the cuffs 34 may be distinct from said absorbent core 46.

Preferably, the containment walls 34 are equipped with elastic members 38, which extend along a substantial length of the containment walls 34. In a common application, the elastic members 38 are placed within the containment walls 34, preferably at the top of the containment walls 34 while in a stretched condition and the glued to the containment walls at least at their ends. When released or otherwise allowed relaxing, the elastic members 38 retract inwardly. When the article 10 is worn, the elastic members 38 function to contract the containment walls 34 about the buttocks and the thighs of the user in a manner, which effects a seal between the article 10, the buttocks and the thighs. The core 46 may be a single sheet of absorbent composite 195 or multilayered, as described above.

FIG. 13 depicts the configuration of the containment walls 34 when it is soft and dry. FIG. 14, on the other hand, depicts the containment walls after wetting, in which the absorbent composite 195 has swollen to dispose the containment walls 34 in a resiliently, erect position. Unlike traditional leg cuffs in the prior art, the resiliently erect containment walls 34 resists flattening (e.g., when the wearer sits down) and, thereby, ensures leakage prevention, especially of explosive, liquefied bowel movements and rapid discharges of urine.

Optional Layers

The disposable absorbent article according to the invention may employ additional layers including an acquisition layer or surge layer 48, preferably situated between the topsheet and the core (e.g., FIG. 10). One function of such an acquisition layer is to spread out or disperse liquid flow so that liquid is distributed more evenly over the core surface. This serves to slow down the flow so that the liquid has adequate time to be absorbed by the core. The acquisition layer also serves to prevent the core from being saturated locally, while a substantial remainder of the core is not absorbing any liquid.

Tape Tabs

The disposable absorbent article must be secured to the wearer. This is most important with respect to diapers since diapers are not pulled up by the wearer, like training pants or incontinent briefs, but are fastened around the wearer. Securing elements compliment the elastic members by effecting a quasi-seal between the wearer and the waistband and leg cuffs, so that liquid is contained within the article which is then absorbed; in other words, so that it does not leak through gaps between the wearer and the edge of the article. The securing elements may be adhesive, mechanical fasteners hook and loop features, or conceivably strings, i.e., anything that will secure one end of the article to the longitudinally opposite end. The securing elements may also be co-adhesive such that they adhere to each other but not other materials.

In the embodiments shown 10 the Figures (see, e.g., FIG. 10), the article 10 is affixed to the wearer by tape fasteners 26 which are permanently affixed to (e.g., sewn directly into) the backsheet 60. Tape fasteners 26 are contacted with the transversely opposite ear 22 extending from the backsheet, where they remain affixed due to adhesive compound applied to the fasteners 26. Alternatively, the article 10 may be training pants, pull-on diapers, and the like. In this configuration, the article 10 mayor may not have tape fasteners 26.

Waistband

Waistbands employing elastic members 52 are positioned along the transverse portion of the article 10 so that when worn, the waistbands are positioned along the waist of the wearer. Generally, the waistband preferably creates a quasi-seal against the waist (transverse elastic members 52) so that liquid waste does not leak from the regions between the waist elastic and the waist of the wearer. The quasi-seal is significant because, although the liquid may be eventually absorbed by filler material, the assault of liquid by the wearer may overwhelm the absorption rate capacity of the filler material. Hence, the waistbands contain the liquid while it is being absorbed. Secondly, the waistbands may have a capacity to absorb liquid (see, e.g., U.S. Pat. No. 5,601,544, which is hereby incorporated by reference).

The present invention is, therefore, well adapted to carry out the objects and attain the ends and the advantages mentioned, as well as others inherent therein. While presently preferred embodiments (in the form of a diaper) have been described, numerous changes to the details of construction, arrangement of the article's parts or components, and the steps to the processes may be made. For example, the various topsheets, backsheet, absorbent core, containment walls and other absorbent composite structures may be utilized in other parts of the article or with other articles other than diapers. Such changes will readily suggest themselves of those skilled in the art and are encompassed within the spirit of invention and in the scope of the appended claims.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of manufacturing a composite sheet, comprising the steps of:
    positioning a first fabric to receive first superabsorbent particles;
    depositing said first superabsorbent particles on said first fabric, whereby said first superabsorbent particles are carried on said first fabric, the first fabric extending in the machine or longitudinal direction, and in the lateral direction transverse to the longitudinal direction;
    positioning a second fabric relative to said first fabric;
    bonding said first fabric to said second fabric along first bond sites, whereby said first superabsorbent particles are secured between said first fabric and said second fabric, whereby said bonding limits particle movement between said first and second fabrics, whereby said first bond sites form a plurality of pockets and said first superabsorbent particles are secured between said first fabric and second fabric in said pockets, thereby forming a first composite sheet extending in the lateral direction and the longitudinal direction and wherein the plurality of pockets are spaced apart in the lateral direction and in the longitudinal direction;
    depositing second superabsorbent particles onto a third fabric;
    bonding said third fabric to a fourth fabric along second bond sites, whereby said second bond sites form a plurality of pockets and said second superabsorbent particles are secured between said third fabric and fourth fabric in said pockets, thereby forming a second composite sheet extending in the lateral direction and the longitudinal direction and wherein the plurality of pockets are spaced apart in the lateral direction and in the longitudinal direction; and
    forming a multi-layer absorbent composite by laminating said first and second composite sheets together;
    whereby, after said bonding of said first fabric to said second fabric and after said forming said multi-layer composite, each of said first fabric and second fabric extends generally laterally and are bonded to each other and a plurality of said pockets are spaced apart in the generally lateral direction in between said first and second fabrics; and
    wherein said bonding the fabrics includes bonding through the superabsorbent particles positioned on one fabric and providing bond sites separating pockets of the superabsorbent particles, and wherein the bond sites form a bonding pattern defining the pockets, wherein the pockets are spaced apart pockets of the superabsorbent particles and wherein the pockets inhibit movement of the superabsorbent particles.

2. The method of claim 1, wherein said bonding along the first and second bond sites forms the bonding pattern including the pockets, and wherein concentrations of said first and second superabsorbent particles positioned in said pockets lack an absorbent matrix.

3. The method of claim 1, wherein said bonding the fabrics includes employing a calendar roll to bond the fabrics along said bond sites and through the superabsorbent particles positioned on one of said fabrics.

4. The method of claim 1, wherein said bonding the fabrics includes ultrasonically bonding one of said fabrics to another of said fabrics along said bond sites and through the superabsorbent particles, wherein the bond sites form the bonding pattern defining the pockets, wherein the pockets are spaced apart pockets of the superabsorbent particles, wherein the pockets inhibit movement of the superabsorbent particles, and wherein the bond sites are arranged to prevent straight line particle migration of more than two inches.

5. The method of claim 1, wherein the superabsorbent particles include loose superabsorbent particles secured in said pockets between said first fabric and said second fabric, said pockets forming a bonding pattern of rectangles.

6. The method of claim 5, wherein said bond sites are discontinuous bond lines.

7. The method of claim 1, wherein said depositing said superabsorbent particles on said first fabric distributes superabsorbent particles thereon and said bonding step bonds through said fabrics and provides a bonding pattern whereby the superabsorbent particles are provided in pockets defined by said bonding pattern.

8. A method for manufacturing an absorbent composite comprising:
    conveying a fabric of nonwoven in the machine direction depositing first superabsorbent particles downward onto a first fabric, whereby a distribution of said particles are provided atop said first fabric;
    bonding said first fabric with said distribution of particles thereon to a second fabric along first bond sites, whereby said first SAP are secured between said first fabric and second fabric to form a first sheet, and wherein the bonding inhibits movement of said first superabsorbent particles;
    depositing second superabsorbent particles onto a third fabric;
    bonding said third fabric to a fourth fabric along second bond sites to from a second sheet, whereby said second superabsorbent particles are secured between said third fabric and said fourth fabric, and whereby the bonding inhibits movement of said second superabsorbent particles;
    depositing third superabsorbent particles onto a fifth fabric;
    bonding said fifth fabric to a sixth fabric along third bond sites to form a third sheet, wherein said third superabsorbent particles are secured between said fifth fabric and said sixth fabric, and wherein the bonding inhibits movement of said third superabsorbent particles; and
    wherein said first, second, and third sheets are positioned adjacent one another to form a multi-layer absorbent composite; and
    wherein said bonding bonds through the first fabric, the second fabric, and the distribution of absorbent particles therebetween, and forms a plurality of pockets across the sheets in the machine-direction and a direction across the sheet transverse to the machine direction; and
    wherein said first, second, or third bond sites form a bonding pattern which forms pockets within which superabsorbent particles are secured and wherein said bonding nudges at least some of the absorbent particles aside.

9. The method of claim 8, wherein each of said first superabsorbent particles, second superabsorbent particles, and third superabsorbent particles comprise concentrations of superabsorbent particles lacking an absorbent matrix.

10. The method of claim 8, wherein said bonding includes forming, with said first, second, or third bond sites, a bonding pattern of rectangles.

11. The method of claim 8, wherein said first, second, or third bond sites are discontinuous bond lines.

12. The method of claim 8, whereby said bonding includes forming said bond sites as discontinuous bond lines.

13. The method of claim 8, wherein said first bond sites form a bonding pattern to secure, between said first and second fabrics, said first superabsorbent particles without an absorbent matrix, said first bond sites forming pockets within which said first superabsorbent particles are positioned; and wherein said first superabsorbent particles include loose superabsorbent particles that are secured between said first fabric and said second fabric.

14. The method of claim 8, wherein each said first, second, and third superabsorbent particles interposed between fabrics form a layer of superabsorbent particles lacking an absorbent matrix.

15. The method of claim 8, wherein bonding said first fabric to said second fabric forms pockets within which said first superabsorbent particles are secured, the pockets inhibiting particle movement, wherein said first bond sites form a bonding pattern of rectangular pockets, and wherein said first bond sites are not aligned in a straight line to lateral margins of the first and second fabrics.

16. The method of claim 8, wherein the second and third fabrics are positioned adjacent one another.

17. The method of claim 16, wherein said bond sites form a plurality of pockets between the fabrics in which said superabsorbent particles are secured, and wherein said super absorbent particles include loose superabsorbent particles secured between the fabrics.

18. The method of claim 8, wherein bonding the first fabric to the second fabric, bonding the third fabric to the fourth fabric, and bonding the fifth fabric to the sixth fabric each comprises bonding via thermal or ultrasonic bonding.

19. The method of claim 8, further comprising aligning said first bond sites with said second bond sites; and wherein bonding said first sheet to said second sheet is along the aligned first and second bond sites.

20. A method for manufacturing an absorbent composite comprising:

depositing first absorbent particles onto a first fabric and providing a distribution of absorbent particles thereon;

bonding a second fabric to said first fabric along first bond sites such that said first absorbent particles are positioned between the first and second fabrics and are limited in movement by said first fabric being bonded to said second fabric along said first bond sites, said absorbent particles lacking an absorbent matrix, whereby said bonding bonds said first fabric through said distribution of particles to said second fabric and nudging absorbent particles aside; and bonding a third fabric to said second fabric at second bond sites such that said second fabric is intermediate said third fabric and said first fabric, wherein second absorbent particles are disposed intermediate the third fabric and the second fabric and lack an absorbent matrix, and wherein the second bond sites inhibit movement of said second absorbent particles, thereby forming a multi-layer absorbent composite.

21. The method of claim 20, wherein said first and second bond sites form bonding patterns and a plurality of pockets within which said absorbent particles are disposed, wherein said bonding pattern is not aligned with the distribution of particles on said first fabric.

22. The method of claim 21, further comprising:

forming a first layer of absorbent particles with said first absorbent particles; and forming a second layer of absorbent particles with said second absorbent particles, wherein concentrations of absorbent particles vary between said layer and said second layer.

23. The method of claim 22, further comprising forming a zone of higher absorbent particle concentration within each said layer of absorbent particles.

24. The method of claim 21, wherein said first, second, and third fabrics are mutually bonded along bond sites extending therethrough.

25. The method of claim 21, wherein said bonding patterns form a pattern of rectangle pockets within which said absorbent particles are disposed.

26. The method of claim 20, wherein said first and second bond sites form a bonding pattern defining spaced apart pockets of said absorbent particles; and wherein the bond sites are arranged prevent straight line particle migration of more than two inches.

27. The method of claim 20, wherein said absorbent particles include loose superabsorbent particles secured between the fabrics and said bond sites form a plurality of pockets between the fabrics within which said superabsorbent particles are positioned.

28. The method of claim 20, wherein said first and second bond sites form bonding patterns and a plurality of pockets within which said absorbent particles are disposed; and wherein said absorbent particles include loose absorbent particles secured in said pockets between said first fabric and said second fabric.

29. The method of claim 20, wherein said bonding includes forming said bond sites, thereby forming a bonding pattern of rectangles, and wherein said bond sites are discontinuous bond lines, wherein said fabrics and layers of said absorbent particles are laminated to form a multi-layer absorbent laminate.

30. A method for manufacturing an absorbent composite comprising:

depositing first superabsorbent particles onto a first fabric being conveyed in the machine direction, whereby the superabsorbent particles are distributed atop thereof in a distribution of particles extending across a sheet of the first fabric in the machine direction and in a direction transverse to the machine direction;

applying a second fabric over the sheet of the first fabric, whereby the distribution of particles are located between the first and second fabric;

bonding said first fabric to the second fabric along first bond sites to form a sandwich with said superabsorbent particles between the fabrics, wherein said first superabsorbent particles are secured between said first fabric and second fabric, and wherein the bonding inhibits movement of said first superabsorbent particles;

depositing second superabsorbent particles onto a third fabric;

bonding said third fabric to a fourth fabric along second bond sites, wherein said second superabsorbent particles are secured between said third fabric and said fourth fabric to form a sandwich with said superabsorbent particles between the fabrics, and wherein the bonding inhibits movement of said second superabsorbent particles;

depositing third superabsorbent particles onto a fifth fabric;

bonding said fifth fabric to a sixth fabric along third bond sites, wherein said third superabsorbent particles are secured between said fifth fabric and said sixth fabric, wherein the bonding inhibits movement of said third superabsorbent particles; and wherein each of said first, second, and third superabsorbent particles comprise concentrations of absorbent material lacking an absorbent matrix, and wherein each of said first, second, and third bond sites forms bonding patterns which form pockets within which said superabsorbent particles are secured; and wherein each of said bonding steps includes embossing between the fabrics and through the distribution of particles therebetween, thereby forming said pockets of said superabsorbent particles, and wherein multiple pockets are located across the sandwich in the machine direction and in a direction transverse to the machine direction and wherein said first, second, or third bond sites form a bonding pattern which forms pockets within which superabsorbent particles are secured and wherein said bonding nudges at least some of the absorbent particles aside.

* * * * *